United States Patent [19]

Blaschke et al.

[11] Patent Number: 4,588,522
[45] Date of Patent: May 13, 1986

[54] BETAINE-AMINE OXIDES, A PROCESS FOR THEIR PREPARATION AND THEIR USE AS SURFACTANTS

[75] Inventors: Günter Blaschke, Winhöring; Alwin Reng, Kelkheim; Jochen M. Quack, Eppstein, all of Fed. Rep. of Germany

[73] Assignee: Hoechst Aktiengesellschaft, Fed. Rep. of Germany

[21] Appl. No.: 484,528

[22] Filed: Apr. 13, 1983

[30] Foreign Application Priority Data

Apr. 24, 1982 [DE] Fed. Rep. of Germany ....... 3215451

[51] Int. Cl.$^4$ .......................... C11D 1/42; C11D 1/18; C07C 135/02; C07C 101/24
[52] U.S. Cl. .................................... 252/547; 252/546; 260/501.13; 564/298
[58] Field of Search .................. 260/501.13; 564/298; 252/6, 7, 357, 547, 546

[56] References Cited

U.S. PATENT DOCUMENTS

| | | | |
|---|---|---|---|
| 3,197,509 | 7/1965 | Drew et al. | 260/583 |
| 3,234,139 | 2/1966 | Drew et al. | 252/137 |
| 3,299,073 | 1/1967 | Wakeman et al. | 260/501.15 |
| 3,431,265 | 3/1969 | Wakeman et al. | 260/501.15 |
| 3,547,986 | 12/1970 | Falcone et al. | 260/501.13 |
| 3,555,079 | 1/1971 | Marumo et al. | 260/501.13 |
| 4,247,424 | 1/1981 | Kuzel et al. | 252/357 |
| 4,338,216 | 7/1982 | Earl et al. | 252/357 |
| 4,399,077 | 8/1983 | Vanlerberghe et al. | 260/501.13 |

FOREIGN PATENT DOCUMENTS

| | | |
|---|---|---|
| 1062392 | 7/1959 | Fed. Rep. of Germany . |
| 1172802 | 6/1964 | Fed. Rep. of Germany . |
| 1249433 | 9/1967 | Fed. Rep. of Germany . |
| 2063422 | 7/1972 | Fed. Rep. of Germany . |
| 2139074 | 8/1976 | Fed. Rep. of Germany . |
| 1361627 | 7/1974 | United Kingdom . |
| 1398276 | 6/1975 | United Kingdom . |
| 1398277 | 6/1975 | United Kingdom . |

OTHER PUBLICATIONS

Morrison et al, *Organic Chem.*, 2nd Ed. Allyn & Bacon, Inc., Boston, pp. 748–749.

Primary Examiner—Glennon H. Hollrah
Assistant Examiner—Raymond Covington
Attorney, Agent, or Firm—Connolly and Hutz

[57] ABSTRACT

Betaine-amine oxides of the formula

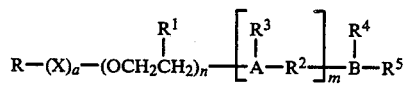

in which R denotes alkyl, alkenyl or hydroxyalkyl, each of which has 8–22 carbon atoms, $R^1$ denotes hydrogen or methyl, $R^2$ denotes ethylene, propylene or 2-hydroxypropylene, $R^3$, $R^4$ and $R^5$ can be identical or different and denote $C_1$–$C_3$-alkyl or a group of the formula

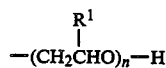

or $R^3$ denotes a group of the formula —$R^2$—$BR^4R^5$, X denotes a direct bond or a group of the formula

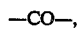

A and B denote a group of the formulae

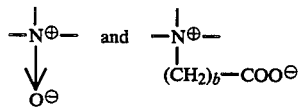

it being necessary for at least one amine oxide group and at least one betaine group to be present, a denotes 0 or 1, b denotes 1, 2 or 3, n denotes a number from 0 to 10 and m denotes 1, 2 or 3. These compounds are obtained by partially quaternizing the parent polyamines with the alkali metal salt of an ω-halogenocarboxylic acid and then oxidizing the non-quaternized nitrogen atoms. These betaine-amine oxides are suitable for use as surfactants in cleansing agents.

5 Claims, No Drawings

BETAINE-AMINE OXIDES, A PROCESS FOR THEIR PREPARATION AND THEIR USE AS SURFACTANTS

It is already known to employ amphoteric surfactants having a betaine group in the molecule, or amine oxides having an amine oxide group in the molecule, on their own or in combination with anionic surfactants in cleansing agents. For example, the use of alkylbetaines in cleansing agents is known from German Auslegeschrift No. 1,249,433, while amidoalkylbetaines are recommended in German Auslegeschrift No. 1,172,802 as bath additives which are tolerated by the skin and in German Auslegeschrift No. 1,537,218 as microbicidal hair-washing agents which do not irritate the eyes. Surfactant mixtures composed of monobetaines and monoamine oxides are also mentioned in German Offenlegungsschrift No. 2,063,422 as advantageous surfactants which are kind to the skin.

Known difunctional amine oxides are the diamine-diamine oxides disclosed in U.S. Pat. Nos. 3,197,509 and 3,234,139. In the way of difunctional dibetaines, polyaminepolybetaines are described, inter alia, in German Auslegeschrift No. 2,139,074 as amphoteric, surface-active cleansing agents in a washing agent composition.

It has been found, however, that neither diamine-diamine oxides nor diaminedibetaines can satisfy the increasing demands made on components of cleansing agents.

It has now been found, surprisingly, that amphoteric surfactants containing one or more amine oxide groups and, at the same time, one or more betaine groups in one molecule have better technical properties in use than the pure amine oxides or betaines or mixtures of the latter with one another.

The invention relates, therefore, to mixed betaine-amine oxides of the formula

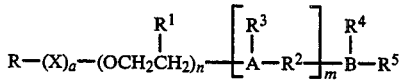

in which R denotes alkyl, alkenyl or hydroxyalkyl, each of which has 8–22, preferably 12–18, carbon atoms, $R^1$ denotes hydrogen or methyl, $R^2$ denotes ethylene, propylene or 2-hydroxypropylene, $R^3$, $R^4$ and $R^5$ can be identical or different and denote $C_1$–$C_3$-alkyl or a group of the formula

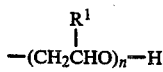

and $R^3$ also denotes the group

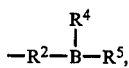

X denotes a direct bond or a group of the formula

—CO—,

A and B denote a group of the formulae

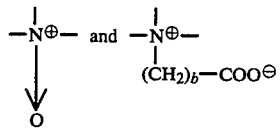

it being necessary for at least one amine oxide group and at least one betaine group to be present, a denotes 0 or 1, b denotes 1, 2 or 3, n denotes a number from 0 to 10 and m denotes 1, 2 or 3.

Preferred compounds are those of the above formula in which $R^1$ denotes hydrogen, $R^2$ denotes propylene or 2-hydroxypropylene, $R^3$, $R^4$ and $R^5$ are identical and denote methyl or hydroxyethyl, a is zero and m is 1 or 2.

These compounds are prepared by quaternizing one mole of a polyamine of the formula

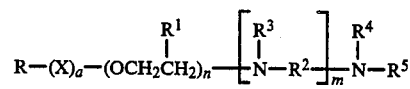

with 1 to 3 moles of an alkali metal salt of an ω-halogenocarboxylic acid of the formula

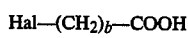

and then oxidizing the resulting betaine with hydrogen peroxide.

The betaine-amine oxides according to the invention are prepared from polyamines containing tertiary nitrogen atoms. These polyamines have already been known for a long time. They are obtained, for example, by reactions carried out on alkylamines or alkylpolyoxethylamines which still contain at least one reactive hydrogen atom on the basic nitrogen atom. Such reactions can be cyanoalkylations with acrylonitrile followed by hydrogenation, which can be repeated several times; aminoalkylations with cyclic amine compounds, such as, for example, aziridine; reaction with ω-halogenoalkyl nitriles or ω-halogenoamines, such as, for example, chloroacetonitrile, chloroethyldimethylamine or chloroethyldiethanolamine; epoxidization reactions with compounds such as ethylene oxide, propylene oxide, glycidol or epichlorohydrin, followed by ammonolysis or aminolysis. The polyamines thus obtained are reacted with customary alkylating agents, such as alkyl halides, formaldehyde, ethylene oxide, propylene oxide or mixtures thereof, to give the tertiary polyamines (see Houben-Weyl, Volume 11/1 et seq. or S. J. Gutcho, Surfactants and Sequestrants, Chem. Techn. Rev. 89). Examples of starting amines which can be employed are the following amines, some of which are also available as commercial products:

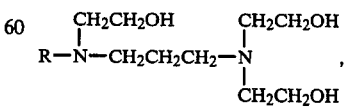

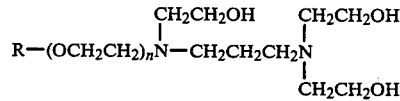

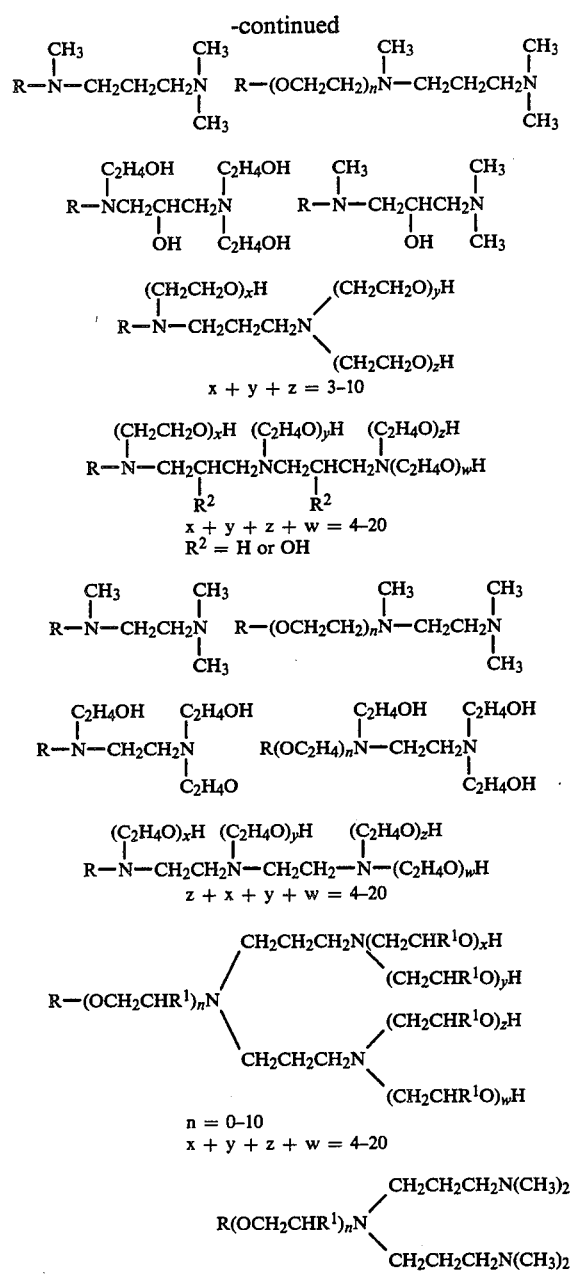

The radical R in these starting compounds and correspondingly also in the end products represents long-chain alkyl, alkenyl or hydroxyalkyl groups, preferably those which are derived from naturally occurring fatty acids composed of linear or branched alkyl chains originating from the Ziegler process (ethylene synthesis alcohols) or from the oxo synthesis. Accordingly, the starting materials and the end products can be mixtures in which the radical R has various meanings, depending on the composition of the particular fatty alkyl mixture. Examples of such mixtures, derived from naturally occurring fatty acids, are tallow fatty alkyl or coconut fatty alkyl.

The compounds according to the invention are obtained from the tertiary polyamines by quaternization with an alkali metal salt of an ω-halogenocarboxylic acid, preferably with the sodium salts of chloroacetic acid, chloropropionic acid, bromoacetic acid or chloro-n-butyric acid. Instead of these alkali metal salts, the reaction can also be carried out by means of the corresponding free acids if an alkali metal hydroxide is added. The quaternization takes place in an aqueous solution at temperatures of approx. 70°–100° C. The ratio between the polyamine and the halogenocarboxylic acid salt is selected in such a way that at least one nitrogen atom in the molecule is quaternized. However, at least one nitrogen atom in the molecule must not be quaternized, but must remain free for the introduction of the amine oxide group. Accordingly, the molar ratio of halogenocarboxylic acid salt to polyamine is 1:1 to 3:1.

It is known that the rate of the quaternization reaction between tertiary amines and—halogenocarboxylic acids or alkali metal salts thereof depends on the basicity, reactivity and steric environment of the tertiary nitrogen atoms, the reaction rate and the degree of reaction of, for example, sodium chloroacetate with a tertiary amine decreasing in the following sequence:

$$R-N(CH_3)_2 > R-N(C_2H_4OH)_2 >> R_2-N-CH_3 > R_2N(C_2H_4OH) >> R_3N.$$

In accordance with this series, terminal tertiary amino groups are quaternized preferentially by the alkali metal salt of an ω-halogenocarboxylic acid, inner tertiary amino groups are only quaternized to a minor extent, since they correspond to an $R_2N(CH_3)$ or $R_2N(C_2H_4OH)$ group.

An alkylpolyaminoalkylbetaine or alkylpolyoxalkyl-polyaminoalkylbetaine is thus obtained as an intermediate stage, preferably in the form of a 30 to 40% strength solution in water. The remaining, non-quaternized tertiary nitrogen of the aminobetaine formed as an intermediate stage is then oxidized at a temperature of 60°–90° C. to give the polyfunctional betaine/amine oxides according to the invention, using 35% strength or 70% strength hydrogen peroxide, which is used in a 5 to 10% molar excess, relative to free tertiary amino groups. It is advantageous to prepare the betaine/amine oxides according to the invention in the form of 30–40% strength aqueous formulations by choosing a suitable water content in the last reaction stage. In addition to the betaine-amine oxides according to the invention, the reaction product can also contain, additionally, varying quantities of polyamines which carry only betaine groups or only amine oxide groups. However, the proportion of these compounds is not critical for practical use.

The betaine-amine oxides according to the invention are used as surfactants in the known and customary cleansing agents, such as, for example, washing agents of all kinds for the hair and the body, household cleansing agents, washing agents for textiles, washing-up liquids, automobile cleansing agents and other industrial cleansing agents. The content of betaine-amine oxide in these cleansing agents is within the limits customary in this respect, that is to say, for instance, between 1 and 50, preferably 5 and 15, % by weight. The nature and amount of other components in these cleansing agents is customary and known and therefore needs no further explanation.

The advantage of the products according to the invention compared with the single-substance polyaminepolybetaines and polyaminepolyoxides is that the foaming behavior, the foam stability, the viscosity, the possibility of thickening by means of electrolytes and alkylsulfates or ether-sulfates, the behavior under cold conditions, the wetting power and the hair-conditioning effects when used in shampoos are improved.

EXAMPLE 1

170.4 g (0.4 mole) of laurylpropylenediaminetrisoxethylate of the formula

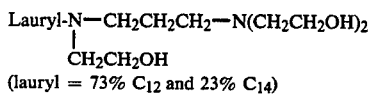

(lauryl = 73% $C_{12}$ and 23% $C_{14}$)

and 318.9 g of water are initially placed in a flask equipped with a reflux condenser, a thermometer, a stirrer and a metering vessel, and are warmed to 90° C., while stirring. 46.6 g (0.4 mole) of sodium chloroacetate in 108.7 g of water are then added at this temperature in the course of one hour, and stirring is continued for 12 hours at 95° C. 23.3 g (0.48 mole) of 70% strength hydrogen peroxide are then added and the mixture is stirred for a further 8 hours at 70° C. The betaine-amine oxide according to the invention is obtained in the form of a 30% strength aqueous solution.

The conversion is checked by determining the amine number and the content of amine oxide and by comparing the content of organically linked chlorine with the total chlorine content, in accordance with customary analytical methods.

EXAMPLE 2

81.6 g of sodium chloroacetate in 190.3 g of water are added to 286.3 g (0.7 mole) of coconut fatty aminopropylaminetrisoxethylate of the formula

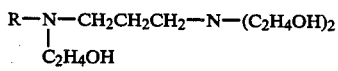

R=6% $C_8$; 6% $C_{10}$; 54% $C_{12}$; 18% $C_{14}$; 8% $C_{16}$ and 8% $C_{18}$) and 530 g of water, and the mixture is stirred for 12 hours at 95° C. It is then oxidized with 40.7 g of 70% strength hydrogen peroxide for 8 hours at 70° C. The betaine-amine oxide is obtained in the form of a 30% strength solution in water.

EXAMPLE 3

619.0 g (1 mole) of coconut alkylpentaoxethylaminopropylaminetrisoxethylate of the formula

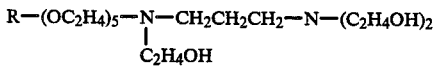

(composition of R as in Example 2) and 1,519.4 g of water are reacted with 116.5 g (1 mole) of sodium chloroacetate for 12 hours at 95° C., and the mixture is then oxidized with 58.3 g of 70% strength hydrogen peroxide to give the corresponding betaine-amine oxide.

EXAMPLE 4

550.0 g (1 mole) of tallow fatty alkyldipropylenetriaminetetrakisoxethylate of the formula

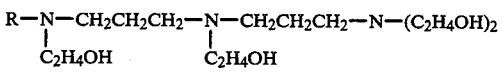

(R=$C_{16}H_{33}$-alkyl and $C_{18}H_{37}$-alkyl) and 1,329.9 g of water are reacted with 233.0 g (2 moles) of sodium chloroacetate for 12 hours at 95° C., and the mixture is then reacted with 116.6 g (2 moles) of 70% strength hydrogen peroxide for 8 hours at 70° C.

A statistical mixture of bisbetaine-amine oxide and betaine-bisamine oxide is obtained in the form of a 30% strength emulsion in water.

EXAMPLE 5

366 g (1 mole) of coconut alkylamino-2-hydroxypropylaminotrisoxethylate of the formula

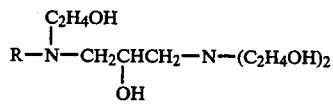

(composition of R as in Example 2) and 929.1 g of water are reacted with 122.3 g (1.05 moles) of sodium chloroacetate for 12 hours at 95° C., and the mixture is then reacted with 68.0 g (1.4 moles) of 70% strength hydrogen peroxide to give the betaine-amine oxide (30% strength in water).

EXAMPLE 6

308.0 g (1 mole) of coconut alkylmethylamino-2-hydroxypropyldimethylamine of the formula

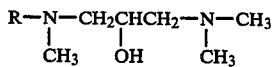

(composition of R as in Example 2) and 793.7 g of water are reacted with 128.2 g (1.1 moles) of $ClCH_2COONa$ for 8 hours at 95° C., and the mixture is then reacted with 53.4 g (1.1 moles) of 70% strength $H_2O_2$ at 70° C. The betaine-amine oxide is obtained in the form of a 30% strength solution in water.

The use examples listed below show the possible ways in which the betaine-amine oxides may be employed in cleansing agents for the hair and the body. Unless otherwise specified, the quantity and percentage figures in the examples relate in each case to weight.

| Hair shampoo with a highlighting effect | |
| --- | --- |
| Betaine-amine oxide prepared in accordance with Example 2 | 15.00% |
| Polyethylene glycol 6000 distearate | 5.20% |
| Perfume oil | 0.30% |
| Formaldehyde | 0.05% |
| Water up to | 100.00% |
| Hair shampoo | |
| Betaine-amine oxide prepared in accordance with Example 2 | 12.00% |
| Hydroxyethylcellulose ether | 1.40% |
| Perfume oil | 0.30% |
| Formaldehyde | 0.05% |
| Water up to | 100.00% |
| Acid shampoo | |
| Betaine-amine oxide prepared in accordance with Example 1 | 15.00% |
| Citric acid | 0.30% |
| Perfume oil | 0.10% |
| Preservatives, dyestuffs and water up to | 100.00% |
| Anti-dandruff shampoo | |
| Betaine-amine oxide prepared in accordance with Example 3 | 5.00% |
| Sodium salt of palm kernel fatty acid methyltauride | 6.00% |
| Sodium salt of stearic acid methyltauride | 4.00% |
| Sodium salt of lauroylsarcoside | 2.00% |
| Zinc salt of 2-mercaptopyridine N—oxide | 0.50% |

| | -continued | |
|---|---|---|
| Perfume oil | | 0.20% |
| Water and dyestuffs up to | | 100.00% |
| Shampoo for greasy hair | | |
| Betaine-amine oxide prepared in accordance with Example 3 | | 7.00% |
| Sodium salt of a secondary alkanesulfate (alkane radical $C_{13}$–$C_{17}$) | | 5.00% |
| Sodium salt of an α-olefin sulfonate ($C_{14}$–$C_{16}$) | | 2.00% |
| Sodium laurylsulfate | | 2.00% |
| Water, preservatives and dyestuffs up to | | 100.00% |
| Shower lotion | | |
| Betaine-amine oxide prepared in accordance with Example 4 | | 12.00% |
| Disodium lauryltetraglycol-ether-sulfosuccinate | | 3.00% |
| Hydroxyethylcellulose ether | | 1.20% |
| Perfume oil | | 0.10% |
| Coconut fatty acid monoethanolamide | | 0.80% |
| Water, preservatives and dyestuffs up to | | 100.00% |
| Bubble bath | | |
| Betaine-amine oxide prepared in accordance with Example 5 | | 5.00% |
| Sodium lauryldiglycol-ether-sulfate | | 20.00% |
| Sodium salt of a secondary alkanesulfonate (alkane radical $C_{13}$–$C_{17}$) | | 5.00% |
| Coconut fatty acid diethanolamide | | 2.00% |
| Perfume oil | | 0.40% |
| Sodium chloride | | 3.00% |
| Water, preservatives and dyestuffs up to | | 100.00% |

FOAM BEHAVIOR

In order to demonstrate the improved foam behavior of the mixed betaine-amine oxides according to the invention, comparison tests were made with the analogous bisbetaines and bisamine oxides according to U.S. Pat. No. 3,197,509 and German Auslegeschrift No. 2,139,074. Since combinations of two or more surfactants are frequently used in practice for commercial reasons, a mixture composed of 7 parts of sodium alkyldiglycol-ether-sulfate (R=75–70% $C_{12}$ and 25–30% $C_{14}$) and 3 parts in each case of the betaine-amine oxide according to Example 2 or 3 parts of the analogous bisbetaine and bisamine oxide was taken here. Measuring the foam height in mm by the Ross-Miles method at 20° of German hardness of water gave the following values for these mixtures:

| Surfactant concentration, % | Betaine-amine oxide according to Example 2 | Bisbetaine | Bisamine-oxide |
|---|---|---|---|
| 1.0 | 270 | 260 | 245 |
| 0.3 | 255 | 240 | 235 |
| 0.1 | 245 | 230 | 215 |
| 0.07 | 225 | 210 | 195 |
| 0.03 | 180 | 165 | 145 |
| 0.01 | — | 105 | — |
| 0.006 | 95 | 60 | 25 |
| 0.002 | 30 | 25 | 15 |

The figures demonstrate the improved effect of the mixed betaine-amine oxides.

We claim:

1. A betaine-amine oxide of the formula

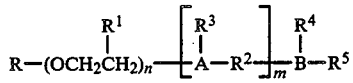

in which R denotes alkyl, alkenyl or hydroxyalkyl, each of which has 8–22, carbon atoms, $R^1$ denotes hydrogen or methyl, $R^2$ denotes ethylene, propylene or 2-hydroxypropylene, $R^3$, $R^4$ and $R^5$ can be identical or different and denote $C_1$–$C_3$-alkyl or a group of the formula

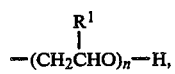

and $R^3$ also denotes the group of the formula —$R^2$—$BR^4R^5$, A and B denote a group of the formulae

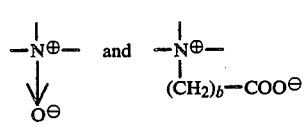

it being necessary for at least one amine oxide group and at least one betaine group to be present, b denotes 1, 2 or 3, n denotes a number from 0 to 10 and m denotes 1, 2 or 3.

2. A betaine-amine oxide as claimed in claim 1, in which $R^1$ denotes hydrogen, $R^2$ denotes propylene or 2-hydroxypropylene, $R^3$, $R^4$ and $R^5$ are identical and denote methyl or hydroxyethyl or $R^3$ denotes a group of the formula —$R^2$—$BR^4R^5$, and m is 2.

3. A betaine-amine oxide as claimed in claim 1, in which R denotes alkyl, alkenyl, or hydroxyalkyl, each of which has 12–18 carbon atoms.

4. A method of cleansing with a cleansing agent composition comprising the step of using an effective amount of a betaine-amine oxide of claim 1 as a surfactant in the cleansing agent composition.

5. A cleansing agent composition comprising an effective amount of a betaine-amine oxide of claim 1 as a surfactant for said cleansing agent composition.

* * * * *